US005976777A

United States Patent [19]

Harder et al.

[11] Patent Number: 5,976,777

[45] Date of Patent: Nov. 2, 1999

[54] PHOTOGRAPHIC ELEMENT CONTAINING MAGENTA COUPLER WITH PARTICULAR SUBSTITUENT

[75] Inventors: John W. Harder, Rocheser; Stanley W. Cowan, Rochester, both of N.Y.; Rakesh Jain, Cupertino, Calif.

[73] Assignee: Eastman Kodak Company, Rochester, N.Y.

[21] Appl. No.: 09/133,882

[22] Filed: Aug. 14, 1998

[51] Int. Cl.[6] .............................. G03C 1/08; G03C 7/26; G03C 7/32

[52] U.S. Cl. .......................... 430/558; 430/543; 430/955

[58] Field of Search .................................... 430/558, 543, 430/955, 957

[56] References Cited

U.S. PATENT DOCUMENTS 4,338,393 7/1982 Bailey et al. .......................... 430/558
5,143,821 9/1992 Crawley et al. ........................ 430/558
5,776,669 7/1998 Crawley et al. ........................ 430/558
5,876,912 3/1999 Crawley et al. ........................ 430/558

FOREIGN PATENT DOCUMENTS 1070030 of 0000 Germany .

*Primary Examiner*—Geraldine Letscher
*Attorney, Agent, or Firm*—Arthur E. Kluegel

[57] ABSTRACT

A photographic element comprises a light-sensitive silver halide emulsion layer having associated therewith a 4-H-pyrazolo-[1,5-a] benzimidazole coupler bearing in the 2-position an alkoxy substituent containing a substituent comprising at least 3 fused carbocyclic rings.

16 Claims, No Drawings

PHOTOGRAPHIC ELEMENT CONTAINING MAGENTA COUPLER WITH PARTICULAR SUBSTITUENT

FIELD OF THE INVENTION

This invention relates to the field of photography and to photographic elements comprising a light-sensitive silver halide emulsion layer having associated therewith a 4-H-pyrazolo-[1,5-a] benzimidazole coupler bearing in the 2-position an alkoxy substituent containing a substituent comprising at least 3 fused carbocyclic rings.

BACKGROUND OF THE INVENTION

Silver halide color photography depends on the formation of dyes in order to reproduce an image. These dyes are typically formed from couplers present in or adjacent to the light sensitive silver halide emulsion layers that react to image light upon exposure. During development, the latent image recorded by the silver halide emulsion is developed to amplify the image. During this process in which silver halide is reduced to elemental silver, the color developer compound used is at the same time oxidized, as is typical in a redox reaction. The oxidized developer then reacts or couples with the coupler compound present in or adjacent to the emulsion layer to form a dye of the desired color.

Typically, a silver halide emulsion layer containing a magenta dye-forming coupler is sensitized to green light. This facilitates so-called negative-positive processing in which the image is initially captured in a negative format where black is captured as white, white as black, and the colors as their complimentary colors (e.g., green as magenta, blue as yellow, and red as cyan). Then the initial image can be optically printed in the correct colors through the device of optical printing which has the effect of producing a negative of the negative, or a positive image of the original scene.

Viewable images may also be produced through reversal processing in which the initial negative color image is reversed by using a black and white developer, processed to remove the developed silver but leave the undeveloped silver halide, and then fogging the element in the presence of color developer to provide developed silver in inverse proportion to the amount of image light with corresponding dye formation.

For incorporation into a photographic element, the couplers are typically dissolved in high-boiling organic solvents known as "coupler solvents," and dispersed in gelatin with the aid of surfactants.

One of the difficulties with color couplers is achieving simultaneously all of the required physical and chemical properties of the coupler and the dye formed from it. For instance, the coupler must have good solubility in the coupler solvent, good dispersibility in gelatin, and high dye-forming activity. It must also have a high degree of stability or resistance to decomposition due to light, heat and humidity, which can cause stains. In addition, the resulting image dye must have the proper hue and must have a high degree of resistance to fading or hue changes due to light, heat and humidity.

Couplers that form magenta dyes upon reaction with oxidized color developing agent are described in such representative patents and publications as: "Farbkuppler-eine Literature Ubersicht," published in Agfa Mitteilungen, Band III, pp. 126–156 (1961) as well as U.S. Pat. Nos. 2,311,082 and 2,369,489; 2,343,701; 2,600,788; 2,908,573; 3,062,653; 3,152,896; 3,519,429; 3,758,309; 3,935,015; 4,540,654; 4,745,052; 4,762,775; 4,791,052; 4,812,576; 4,835,094; 4,840,877; 4,845,022; 4,853,319; 4,868,099; 4,865,960; 4,871,652; 4,876,182; 4,892,805; 4,900,657; 4,910,124; 4,914,013; 4,921,968; 4,929,540; 4,933,465; 4,942,116; 4,942,117; 4,942,118; 4,959,480; 4,968,594; 4,988,614; 4,992,361; 5,002,864; 5,021,325; 5,066,575; 5,068,171; 5,071,739; 5,100,772; 5,110,942; 5,116,990; 5,118,812; 5,134,059; 5,155,016; 5,183,728; 5,234,805; 5,235,058; 5,250,400; 5,254,446; 5,262,292; 5,300,407; 5,302,496; 5,336,593; 5,350,667; 5,395,968; 5,354,826; 5,358,829; 5,368,998; 5,378,587; 5,409,808; 5,411,841; 5,418,123; 5,424,179; EPO 0 257 854; EPO 0 284 240; EPO 0 341 204; EPO 347,235; EPO 365,252; EPO 0 422 595; EPO 0 428 899; EPO 0 428 902; EPO 0459 331; EPO 0 467 327; EPO 0 476 949; EPO 0 487 081; EPO 0 489 333; EPO 0512 304; EPO 0 515 128; EPO 534 703; EPO 0 554 778; EPO 0558 145; EPO 0 571 959; EPO 0 583 832; EPO 0 583 834; EPO 0 584 793; EPO 0 602 748; EPO 0 602 749; EPO 0 605 918; EPO 0 622 672; EPO 0 622 673; EPO 0 629 912; EPO 0 646 841, EPO 0 656 561; EPO 0 660 177; EPO 0 686 872; WO 90/10253; WO 92/09010; WO 92/10788; WO 92/12464; WO 93/01523; WO 93/02392; WO 93/02393; WO 93/07534; UK Application 2,244,053; Japanese Application 03192-350; German OLS 3,624,103; German OLS 3,912,265; and German OLS 40 08 067. Typically, such couplers are pyrazolones and pyrazoloazoles, including pyrazolo[2,3-b][1,2,4]triazoles) described by Formula (A) and pyrazolo [3,2-c][1,2,4]triazoles described by Formula (B).

(A)

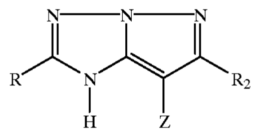

(B)

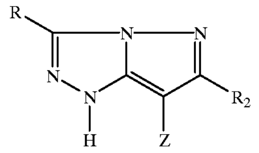

In Formulas (A) and (B), R and $R_2$ represent substituents and Z is a hydrogen atom or a group capable of being split off during the coupling reaction. Typically, $R_2$ is an alkyl group. An alkoxy group in this position leads to image dyes with very poor light stability.

The present invention is concerned with 4H-pyrazolo[1,5-a]benzimidazole type of magenta dye-forming couplers (hereinafter referred to as PBI couplers). These couplers may broadly be described by Formula (1)

(C)

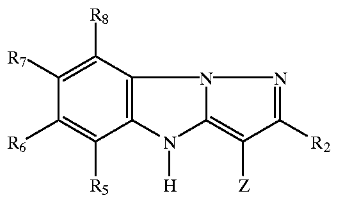

in which $R_2$ and $R_5$–$R_6$ represent substituents and Z represents a hydrogen atom or a group capable of being split off during the coupling reaction. German patent 1,070,030 discloses PBI couplers that form magenta dyes upon coupling. In the examples given, $R_2$ represents an alkyl or phenyl group. Couplers of these types have been found to have poor coupling reactivity, to yield image dyes whose absorption spectra are too bathochromic for practical use in color photographic papers, and to have poor stability to light. International Patent Application WO 91/14970 describes PBI couplers with specifically substituted alkylthio coupling-off groups, including carboxyalkylthio groups. Such couplers offer marked improvements in coupling reactivity but do not offer improved dye hue or light stability. U.S. Pat. No. 5,143,821 describes PBI couplers in which $R_2$ represents an alkoxy group. Such couplers are advantageous because they have much better coupling reactivity than those in which $R_2$ represents an alkyl group and the image dyes formed from them have good spectral absorption characteristics. Moreover, the dyes from these couplers have better light stability than the dyes from PBI couplers in which $R_2$ is an alkyl group. However, the tendency to yellow of these alkoxy PBI couplers is unacceptable for the formation of accurate image reproductions, especially for color photographic papers.

A problem to be solved is to provide a PBI magenta dye forming coupler that exhibits acceptable yellowing characteristics.

SUMMARY OF THE INVENTION

The invention provides a photographic element comprising a light-sensitive silver halide emulsion layer having associated therewith a 4-H-pyrazolo-[1,5-a] benzimidazole coupler bearing in the 2-position an alkoxy substituent containing a substituent comprising at least 3 fused carbocyclic rings.

The element exhibits improved resistance to yellowing.

DETAILED DESCRIPTION OF THE INVENTION

The invention provides a photographic element comprising a light-sensitive silver halide emulsion layer having associated therewith a 4-H-pyrazolo-[1,5-a] benzimidazole coupler bearing in the 2-position an alkoxy substituent containing a substituent comprising at least 3 fused carbocyclic rings. The coupler useful in the invention may be represented by the following formula I:

I

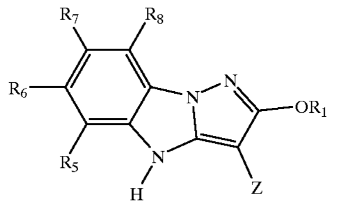

wherein:

$R_1$ is an alkyl group branched at the alpha carbon and contains a substituent comprising three or more fused rings;

$R_5$, $R_6$, $R_7$, and $R_8$ are each independently a hydrogen atom or a substituent; and Z is H or a coupling-off group.

In formula (I), $R_1$ is an alkyl group including linear, branched, or cyclic; saturated or unsaturated groups. Groups are defined hereinafter to include substituted or unsubstituted forms of substitutable groups. Preferably, $R_1$ represents an alkyl group in which the first carbon atom has no more than one hydrogen atom attached; that is, a secondary, tertiary or cyclic alkyl group. Any substituent may be used on $R_1$ provided they are not incompatible with the intended use of the coupler. Examples of such groups include, but are not limited to, an alkyl group, an aryl group, a halogen atom (e.g., Cl, Br or F), a nitro group, a cyano group, a hydroxyl group, an alkoxy group, a sulfonyl group, a sulfamoyl group, a carbamoyl group, a carbonamido group, a sulfonamido group, a carboxy group, a carboalkoxy or carboaryloxy group, an amino group, an alkylthio group, and an arylthio group. Most preferably, RI represents a secondary, tertiary, or cyclic alkyl group.

$R_1$ must comprise a fused substituent of at least three carbocyclic rings. Such rings may comprise 5 or 6 members each and may be saturated or unsaturated. Compounds based on perhydrophenanthrene, such as Steroid compounds, are useful as $R_1$.

In Formula (I), each of $R_5$, $R_6$, $R_7$, and $R_8$ is independently a hydrogen atom or a substituent. Preferably, each of $R_5$, $R_6$, $R_7$, and $R_8$ is a hydrogen atom.

In Formula (I), Z is a hydrogen atom or a group that can be split off by the reaction of the coupler with an oxidized color developing agent, known in the art as a "coupling-off" group. Typical coupling-off groups are halogen atoms and aliphatic, aromatic or heterocyclic groups attached to the coupling site by means of an oxygen, sulfur or nitrogen atom. Suitably, Z is an alkylthio group which may be substituted as described in International Patent Application WO 91/14970. Most preferably, Z is a carboxyalkylthio group.

The following are examples of couplers useful in the invention:

I1

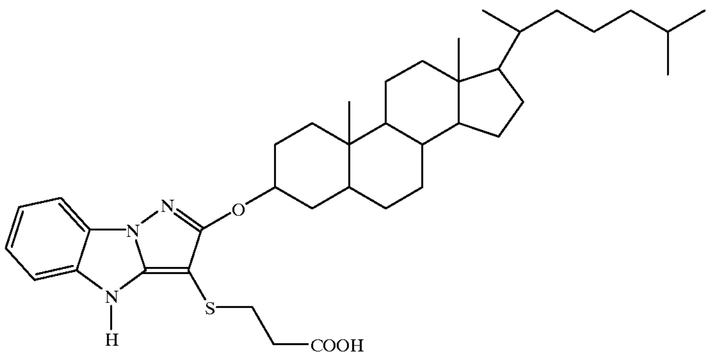

-continued
I2
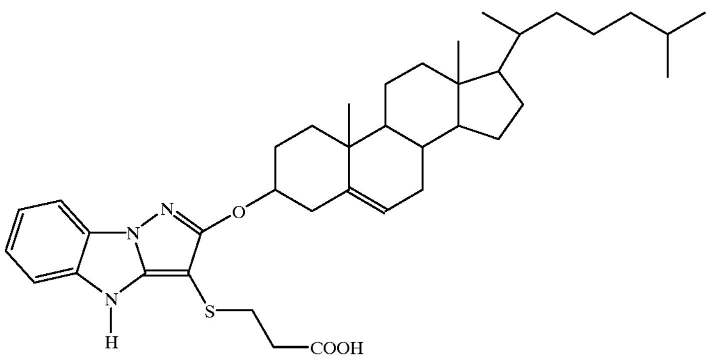
I3
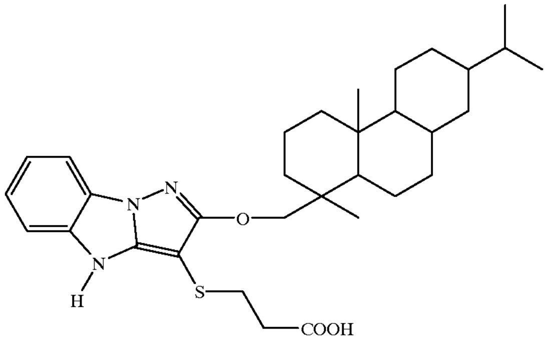
I4
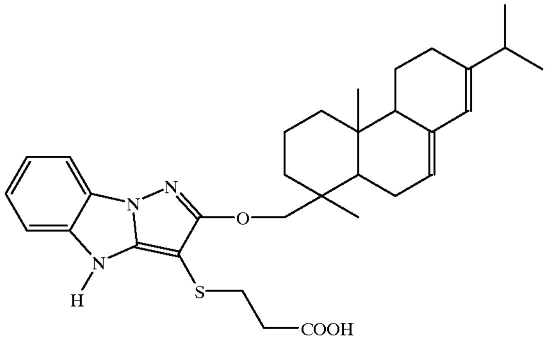
I5
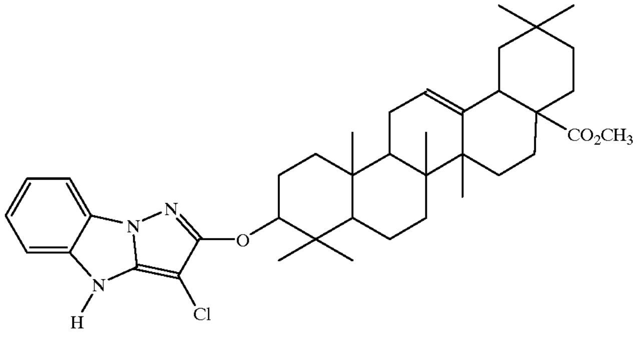

-continued
I6
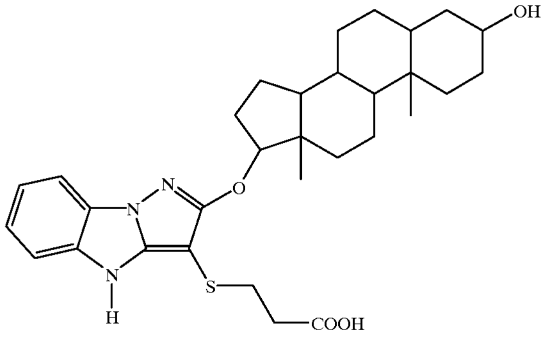
I7
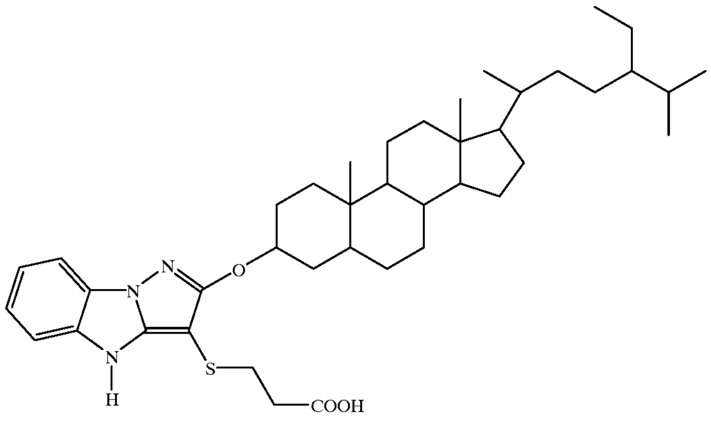
I8
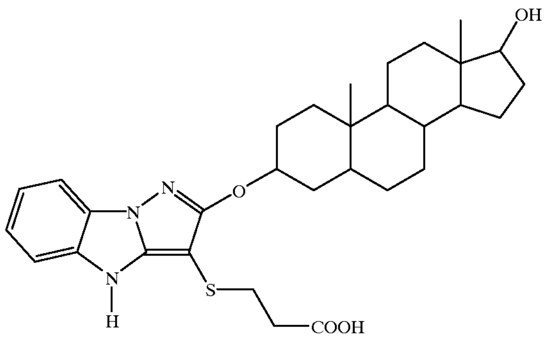
I9
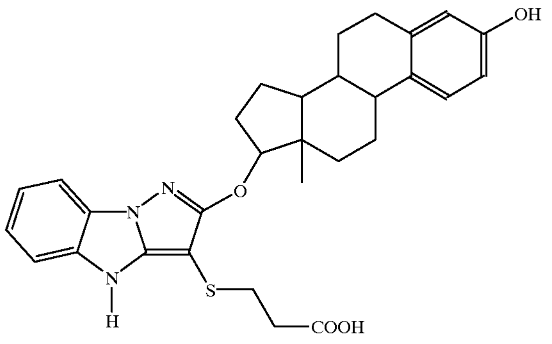

-continued
I10
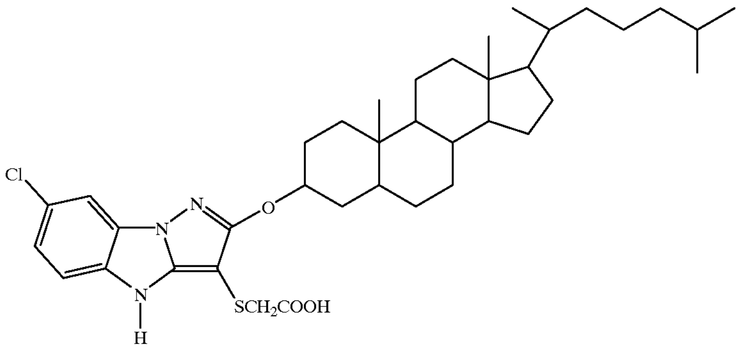
I11
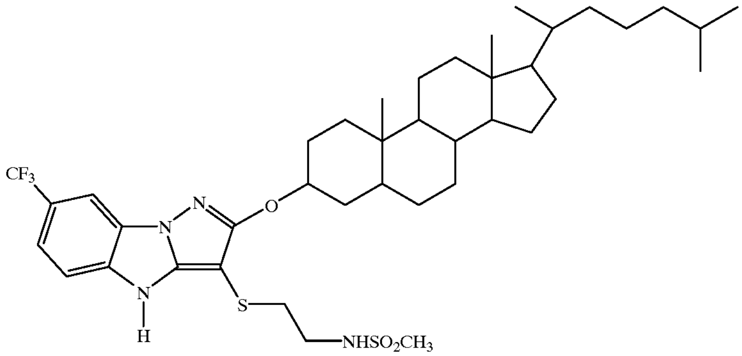
I12
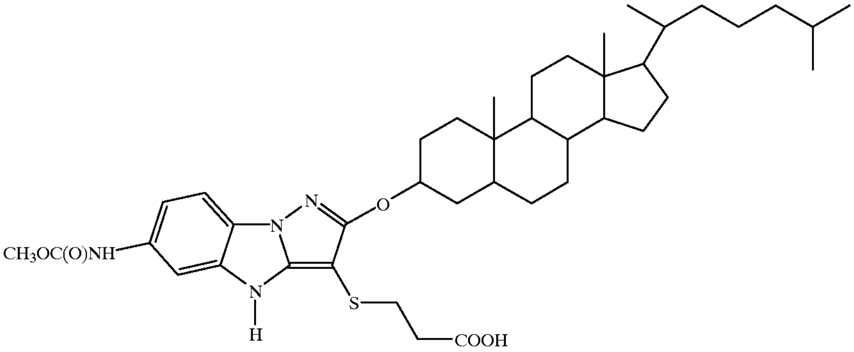
I13
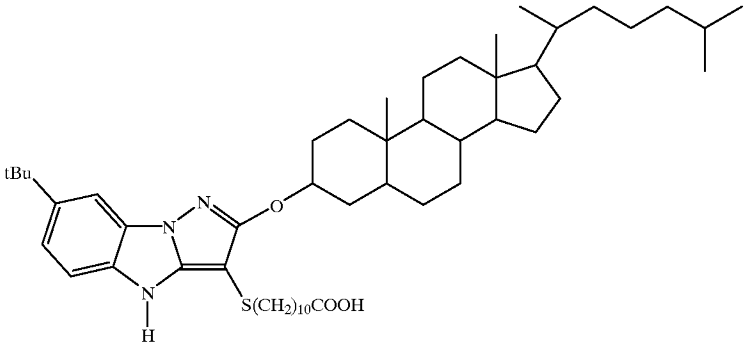
and

-continued

I14

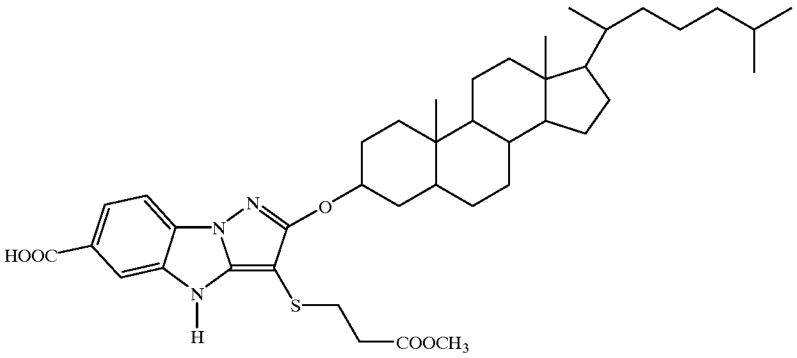

Unless otherwise specifically stated, the term substituted or substituent means any group or atom other than hydrogen bonded to the remainder of a molecule. Additionally, when the term "group" is used, it means that when a substituent group contains a substitutable hydrogen, it is also intended to encompass not only the substituent's unsubstituted form, but also its form further substituted with any substituent group or groups as herein mentioned, so long as the substituent does not destroy properties necessary for photographic utility. Suitably, a substituent group may be halogen or may be bonded to the remainder of the molecule by an atom of carbon, silicon, oxygen, nitrogen, phosphorous, or sulfur. The substituent may be, for example, halogen, such as chlorine, bromine or fluorine; nitro; hydroxyl; cyano; carboxyl; or groups which may be further substituted, such as alkyl, including straight or branched chain or cyclic alkyl, such as methyl, trifluoromethyl, ethyl, t-butyl, 3-(2,4-di-t-pentylphenoxy) propyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy) ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentyl-phenoxy)acetamido, alpha-(2,4-di-t-pentylphenoxy) butyramido, alpha-(3-pentadecylphenoxy)-hexanamido, alpha-(4-hydroxy-3-t-butylphenoxy)-tetradecanamido, 2-oxo-pyrrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl) carbonylamino, p-dodecylphenylcarbonylamino, p-tolylcarbonylamino, N-methylureido, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-p-tolylureido, N-(m-hexadecylphenyl)ureido, N,N-(2,5-di-t-pentylphenyl)-N'-ethylureido, and t-butylcarbonamido; sulfonamido, such as methylsulfonamido, benzenesulfonamido, p-tolylsulfonamido, p-dodecylbenzenesulfonamido, N-methyltetradecylsulfonamido, N,N-dipropyl-sulfamoylamino, and hexadecylsulfonamido; sulfamoyl, such as N-methylsulfamoyl, N-ethylsulfamoyl, N,N-dipropylsulfamoyl, N-hexadecylsulfamoyl, N,N-dimethylsulfamoyl; N-[3-(dodecyloxy)propyl] sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; acyl, such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-tolylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-tolylsulfinyl; thio, such as ethylthio, octylthio, benzylthio, tetradecylthio, 2-(2,4-di-t-pentylphenoxy)ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1 (N-phenylimido)ethyl, N-succinimido or 3-benzylhydantoinyl; phosphate, such as dimethylphosphate and ethylbutylphosphate; phosphite, such as diethyl and dihexylphosphite; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, such as 2-furyl, 2-thienyl, 2-benzimidazolyloxy or 2-benzothiazolyl; quaternary ammonium, such as triethylammonium; and silyloxy, such as trimethylsilyloxy.

If desired, the substituents may themselves be further substituted one or more times with the described substituent groups. The particular substituents used may be selected by those skilled in the art to attain the desired photographic properties for a specific application and can include, for example, hydrophobic groups, solubilizing groups, blocking groups, releasing or releasable groups, etc. Generally, the above groups and substituents thereof may include those having up to 48 carbon atoms, typically 1 to 36 carbon atoms and usually less than 24 carbon atoms, but greater numbers are possible depending on the particular substituents selected.

The materials of the invention can be used in any of the ways and in any of the combinations known in the art. Typically, the invention materials are incorporated in a silver halide emulsion and the emulsion coated as a layer on a support to form part of a photographic element. Alternatively, they can be incorporated at a location adjacent to the silver halide emulsion layer where, during development, they will be in reactive association with development products such as oxidized color developing agent. Thus, as used herein, the term "associated" signifies that the compound is in the silver halide emulsion layer or in an adjacent location where, during processing, it is capable of reacting with silver halide development products.

To control the migration of various components, it may be desirable to include a high molecular weight hydrophobe or "ballast" group in the component molecule. Representative ballast groups include substituted or unsubstituted alkyl or aryl groups containing 8 to 40 carbon atoms. Representative substituents on such groups include alkyl, aryl, alkoxy, aryloxy, alkylthio, hydroxy, halogen, alkoxycarbonyl, aryloxcarbonyl, carboxy, acyl, acyloxy, amino, anilino, carbonamido, carbamoyl, alkylsulfonyl, arysulfonyl, sulfonamido, and sulfamoyl groups wherein the substituents typically contain 1 to 40 carbon atoms. Such substituents can also be further substituted.

The photographic elements can be single color elements or multicolor elements. Multicolor elements contain image dye-forming units sensitive to each of the three primary regions of the spectrum. Each unit can comprise a single emulsion layer or multiple emulsion layers sensitive to a given region of the spectrum. The layers of the element, including the layers of the image-forming units, can be arranged in various orders as known in the art. In an alternative format, the emulsions sensitive to each of the three primary regions of the spectrum can be disposed as a single segmented layer.

A typical multicolor photographic element comprises a support bearing a cyan dye image-forming unit comprised of at least one red-sensitive silver halide emulsion layer having associated therewith at least one cyan dye-forming coupler, a magenta dye image-forming unit comprising at least one green-sensitive silver halide emulsion layer having associated therewith at least one magenta dye-forming coupler, and a yellow dye image-forming unit comprising at least one blue-sensitive silver halide emulsion layer having associated therewith at least one yellow dye-forming coupler. The element can contain additional layers, such as filter layers, interlayers, overcoat layers, subbing layers, and the like.

If desired, the photographic element can be used in conjunction with an applied magnetic layer as described in *Research Disclosure,* November, 1992, Item 34390 published by Kenneth Mason Publications, Ltd., Dudley Annex, 12a North Street, Emsworth, Hampshire P010 7DQ, ENGLAND, or as described in Hatsumi Kyoukai Koukai Gihou No. 94-6023, published Mar. 15, 1994, available from the Japanese Patent Office, the contents of which are incorporated herein by reference.

In the following discussion of suitable materials for use in the emulsions and elements of this invention, reference will be made to *Research Disclosure,* Sep. 1996, Item 38957, available as described above, which will be identified hereafter by the term "Research Disclosure". The contents of the Research Disclosure, including the patents and publications referenced therein, are incorporated herein by reference, and the Sections hereafter referred to are Sections of the Research Disclosure.

The silver halide emulsions employed in the elements of this invention can be either negative-working or positive-working. Suitable emulsions and their preparation as well as methods of chemical and spectral sensitization are described in Sections I through V. Various additives such as UV dyes, brighteners, antifoggants, stabilizers, light absorbing and scattering materials, and physical property modifying addenda such as hardeners, coating aids, plasticizers, lubricants and matting agents are described, for example, in Sections II and VI through VIII. Color materials are described in Sections X through XIII. Suitable methods for incorporating couplers and dyes, including dispersions in organic solvents, are described in Section X(E). Scan facilitating is described in Section XIV. Supports, exposure, development systems, and processing methods and agents are described in Sections XV to XX. Certain desirable photographic elements and processing steps are described in *Research Disclosure,* Item 37038, February, 1995.

Coupling-off groups are well known in the art. Such groups can determine the chemical equivalency of a coupler, i.e., whether it is a 2-equivalent or a 4-equivalent coupler, or modify the reactivity of the coupler. Such groups can advantageously affect the layer in which the coupler is coated, or other layers in the photographic recording material, by performing, after release from the coupler, functions such as dye formation, dye hue adjustment, development acceleration or inhibition, bleach acceleration or inhibition, electron transfer facilitation, color correction and the like.

The presence of hydrogen at the coupling site provides a 4-equivalent coupler, and the presence of another coupling-off group usually provides a 2-equivalent coupler. Representative classes of such coupling-off groups include, for example, chloro, alkoxy, aryloxy, hetero-oxy, sulfonyloxy, acyloxy, acyl, heterocyclyl such as oxazolidinyl or hydantoinyl, sulfonamido, mercaptotetrazole, benzothiazole, mercaptopropionic acid, phosphonyloxy, arylthio, and arylazo. These coupling-off groups are described in the art, for example, in U.S. Pat. Nos. 2,455,169, 3,227,551, 3,432,521, 3,476,563, 3,617,291, 3,880,661, 4,052,212 and 4,134,766; and in U.K. Patents and published application Nos. 1,466,728, 1,531,927, 1,533,039, 2,006,755A and 2,017,704A, the disclosures of which are incorporated herein by reference.

Image dye-forming couplers may be included in the element such as couplers that form cyan dyes upon reaction with oxidized color developing agents which are described in such representative patents and publications as: "Farbkuppler-eine Literature Ubersicht," published in Agfa Mitteilungen, Band III, pp. 156–175 (1961) as well as in U.S. Pat. Nos. 2,367,531; 2,423,730; 2,474,293; 2,772,162; 2,895,826; 3,002,836; 3,034,892; 3,041,236; 4,333,999; 4,746,602; 4,753,871; 4,770,988; 4,775,616; 4,818,667; 4,818,672; 4,822,729; 4,839,267; 4,840,883; 4,849,328; 4,865,961; 4,873,183; 4,883,746; 4,900,656; 4,904,575; 4,916,051; 4,921,783; 4,923,791; 4,950,585; 4,971,898; 4,990,436; 4,996,139; 5,008,180; 5,015,565; 5,011,765; 5,011,766; 5,017,467; 5,045,442; 5,051,347; 5,061,613; 5,071,737; 5,075,207; 5,091,297; 5,094,938; 5,104,783; 5,178,993; 5,813,729; 5,187,057; 5,192,651; 5,200,305 5,202,224; 5,206,130; 5,208,141; 5,210,011; 5,215,871; 5,223,386; 5,227,287; 5,256,526; 5,258,270; 5,272,051; 5,306,610; 5,326,682; 5,366,856; 5,378,596; 5,380,638; 5,382,502; 5,384,236; 5,397,691; 5,415,990; 5,434,034; 5,441,863; EPO 0 246 616; EPO 0 250 201; EPO 0 271 323;

EPO 0 295 632; EPO 0 307 927; EPO 0 333 185; EPO 0 378 898; EPO 0 389 817; EPO 0 487 111; EPO 0 488 248; EPO 0 539 034; EPO 0 545 300; EPO 0 556 700; EPO 0 556 777; EPO 0 556 858; EPO 0 569 979; EPO 0 608 133; EPO 0 636 936; EPO 0 651 286; EPO 0 690 344; German OLS 4,026,903; German OLS 3,624,777. and German OLS 3,823,049. Typically such couplers are phenols, naphthols, or pyrazoloazoles.

Couplers that form yellow dyes upon reaction with oxidized color developing agent are described in such representative patents and publications as: "Farbkuppler-eine Literature Ubersicht," published in Agfa Mitteilungen; Band III; pp. 112–126 (1961); as well as U.S. Pat. No. 2,298,443; 2,407,210; 2,875,057; 3,048,194; 3,265,506; 3,447,928; 4,022,620; 4,443,536; 4,758,501; 4,791,050; 4,824,771; 4,824,773; 4,855,222; 4,978,605; 4,992,360; 4,994,361; 5,021,333; 5,053,325; 5,066,574; 5,066,576; 5,100,773; 5,118,599; 5,143,823; 5,187,055; 5,190,848; 5,213,958; 5,215,877; 5,215,878; 5,217,857; 5,219,716; 5,238,803; 5,283,166; 5,294,531; 5,306,609; 5,328,818; 5,336,591; 5,338,654; 5,358,835; 5,358,838; 5,360,713; 5,362,617; 5,382,506; 5,389,504; 5,399,474; 5,405,737; 5,411,848; 5,427,898; EPO 0 327 976; EPO 0 296 793; EPO 0 365 282; EPO 0 379 309; EPO 0 415 375; EPO 0 437 818; EPO 0 447 969; EPO 0 542 463;EPO 0 568 037; EPO 0 568 196; EPO 0 568 777; EPO 0 570 006; EPO 0 573 761; EPO 0 608 956; EPO 0 608 957; and EPO 0 628 865. Such couplers are typically open chain ketomethylene compounds.

Couplers that form colorless products upon reaction with oxidized color developing agent are described in such representative patents as: U.K. Patent No. 861,138; U.S. Pat. Nos. 3,632,345, 3,928,041, 3,958,993 and 3,961,959. Typically such couplers are cyclic carbonyl containing compounds that form colorless products on reaction with an oxidized color developing agent.

Couplers that form black dyes upon reaction with oxidized color developing agent are described in such representative patents as U.S. Pat. Nos. 1,939,231; 2,181,944; 2,333,106; and 4,126,461; German OLS No. 2,644,194 and German OLS No. 2,650,764. Typically, such couplers are resorcinols or m-aminophenols that form black or neutral products on reaction with oxidized color developing agent.

It may be useful to use a combination of couplers any of which may contain known ballasts or coupling-off groups such as those described in U.S. Pat. No. 4,301,235; U.S. Pat. No. 4,853,319 and U.S. Pat. No. 4,351,897. The coupler may contain solubilizing groups such as described in U.S. Pat. No. 4,482,629.

Typically, couplers are incorporated in a silver halide emulsion layer in a mole ratio to silver of 0.1 to 1.0 and generally 0.1 to 0.5. Usually the couplers are dispersed in a high-boiling organic solvent in a weight ratio of solvent to coupler of 0.1 to 10.0, typically 0.1 to 2.0 and usually 0.1 to 0.6, although direct dispersions are sometimes employed.

The invention materials may also be used in association with materials that accelerate or otherwise modify the processing steps e.g. of bleaching or fixing to improve the quality of the image. Bleach accelerator releasing couplers such as those described in EP 193,389; EP 301,477; U.S. Pat. No. 4,163,669; U.S. Pat. No. 4,865,956; and U.S. Pat. No. 4,923,784 may be useful. Also contemplated is use of the compositions in association with nucleating agents, development accelerators or their precursors (UK Patent 2,097,140; U.K. Patent 2,131,188); electron transfer agents (U.S. Pat. No. 4,859,578; U.S. Pat. No. 4,912,025); antifogging and anti color-mixing agents such as derivatives of hydroquinones, aminophenols, amines, gallic acid; catechol; ascorbic acid; hydrazides; sulfonamidophenols; and non color-forming couplers.

It is contemplated that the concepts of the present invention may be employed to obtain reflection color prints as described in *Research Disclosure,* November, 1979, Item 18716, available from Kenneth Mason Publications, Ltd, Dudley Annex, 12a North Street, Emsworth, Hampshire P0101 7DQ, England, incorporated herein by reference. Materials of the invention may be coated on pH adjusted support as described in U.S. Pat. No. 4,917,994; on a support with reduced oxygen permeability (EP 553,339); with epoxy solvents (EP 164,961); with nickel complex stabilizers (U.S. Pat. No. 4,346,165; U.S. Pat. No. 4,540,653 and U.S. Pat. No. 4,906,559 for example); with ballasted chelating agents such as those in U.S. Pat. No. 4,994,359 to reduce sensitivity to polyvalent cations such as calcium; and with stain reducing compounds such as described in U.S. Pat. No. 5,068,171. Other compounds useful in combination with the invention are disclosed in Japanese Published Applications described in Derwent Abstracts having accession numbers as follows: 90-072,629, 90-072,630; 90-072,631; 90-072,632; 90-072,633; 90-072,634; 90-077,822; 90- 078,229; 90-078,230; 90-079,336; 90-079,337; 90-079,338; 90-079,690; 90-079,691; 90-080,487; 90-080,488; 90-080,489; 90-080,490; 90-080,491; 90-080,492; 90-080,494; 90-085,928; 90-086,669; 90-086,670; 90-087,360; 90-087,361; 90-087,362; 90-087,363; 90-087,364; 90-088,097; 90-093,662; 90-093,663; 90-093,664; 90-093,665; 90-093,666; 90-093,668; 90-094,055; 90-094,056; 90-103,409; 83-62,586; 83-09,959.

Conventional radiation-sensitive silver halide emulsions can be employed in the practice of this invention. Such emulsions are illustrated by *Research Disclosure,* Item 38755, September, 1996, 1. Emulsion grains and their preparation.

Especially useful in this invention are tabular grain silver halide emulsions. Tabular grains are those having two parallel major crystal faces and having an aspect ratio of at least 2. The term "aspect ratio" is the ratio of the equivalent circular diameter (ECD) of a grain major face divided by its thickness (t). Tabular grain emulsions are those in which the tabular grains account for at least 50 percent (preferably at least 70 percent and optimally at least 90 percent) of total grain projected area. Preferred tabular grain emulsions are those in which the average thickness of the tabular grains is less than 0.3 micrometer (preferably thin—that is, less than 0.2 micrometer and most preferably ultrathin—that is, less than 0.07 micrometer). The major faces of the tabular grains can lie in either {111} or {100} crystal planes. The mean ECD of tabular grain emulsions rarely exceeds 10 micrometers and more typically is less than 5 micrometers.

In their most widely used form tabular grain emulsions are high bromide {111} tabular grain emulsions. Such emulsions are illustrated by Kofron et al U.S. Pat. No. 4,439,520, Wilgus et al U.S. Pat. No. 4,434,226, Solberg et al U.S. Pat. No. 4,433,048, Maskasky U.S. Pat. Nos. 4,435,501, 4,463,087 and 4,173,320, Daubendiek et al U.S. Pat. Nos. 4,414,310 and 4,914,014, Sowinski et al U.S. Pat. No. 4,656,122, Piggin et al U.S. Pat. Nos. 5,061,616 and 5,061,609, Tsaur et al U.S. Pat. Nos. 5,147,771, '772, '773, 5,171,659 and 5,252,453, Black et al U.S. Pat. No. 5,219,720 and 5,334,495, Delton U.S. Pat. Nos. 5,310,644, 5,372,927 and 5,460,934, Wen U.S. Pat. No. 5,470,698, Fenton et al U.S. Pat. No. 5,476,760, Eshelman et al U.S. Pat. Nos. 5,612,175 and 5,614,359, and Irving et al U.S. Pat. No. 5,667,954.

Ultrathin high bromide {111} tabular grain emulsions are illustrated by Daubendiek et al U.S. Pat. Nos. 4,672,027, 4,693,964, 5,494,789, 5,503,971 and 5,576,168, Antoniades et al U.S. Pat. No. 5,250,403, Olm et al U.S. Pat. No. 5,503,970, Deaton et al U.S. Pat. No. 5,582,965, and Maskasky U.S. Pat. No. 5,667,955.

High bromide {100} tabular grain emulsions are illustrated by Mignot U.S. Pat. Nos. 4,386,156 and 5,386,156.

High chloride {111} tabular grain emulsions are illustrated by Wey U.S. Pat. No. 4,399,215, Wey et al U.S. Pat. No. 4,414,306, Maskasky U.S. Pat. Nos. 4,400,463, 4,713,323, 5,061,617, 5,178,997, 5,183,732, 5,185,239, 5,399,478 and 5,411,852, and Maskasky et al U.S. Pat. Nos. 5,176,992 and 5,178,998. Ultrathin high chloride {111} tabular grain emulsions are illustrated by Maskasky U.S. Pat. Nos. 5,271,858 and 5,389,509.

High chloride {100} tabular grain emulsions are illustrated by Maskasky U.S. Pat. Nos. 5,264,337, 5,292,632, 5,275,930 and 5,399,477, House et al U.S. Pat. No. 5,320,938, Brust et al U.S. Pat. No. 5,314,798, Szajewski et al U.S. Pat. No. 5,356,764, Chang et al U.S. Pat. Nos. 5,413,904 and 5,663,041, Oyamada U.S. Pat. No. 5,593,821, Yamashita et al U.S. Pat. Nos. 5,641,620 and 5,652,088, Saitou et al U.S. Pat. No. 5,652,089, and Oyamada et al U.S. Pat. No. 5,665,530. Ultrathin high chloride {100} tabular grain emulsions can be prepared by nucleation in the presence of iodide, following the teaching of House et al and Chang et al, cited above.

The emulsions can be surface-sensitive emulsions, i.e., emulsions that form latent images primarily on the surfaces of the silver halide grains, or the emulsions can form internal latent images predominantly in the interior of the silver halide grains. The emulsions can be negative-working emulsions, such as surface-sensitive emulsions or unfogged internal latent image-forming emulsions, or direct-positive emulsions of the unfogged, internal latent image-forming type, which are positive-working when development is conducted with uniform light exposure or in the presence of a nucleating agent. Tabular grain emulsions of the latter type are illustraed by Evans et al. U.S. Pat. No. 4,504,570.

Photographic elements can be exposed to actinic radiation, typically in the visible region of the spectrum, to form a latent image and can then be processed to form a visible dye image. Processing to form a visible dye image includes the step of contacting the element with a color developing agent to reduce developable silver halide and oxidize the color developing agent. Oxidized color developing agent in turn reacts with the coupler to yield a dye. If desired "Redox Amplification" as described in Research Disclosure XVIII-B(5) may be used.

With negative-working silver halide, the processing step described above provides a negative image. One type of such element, referred to as a color negative film, is designed for image capture. Speed (the sensitivity of the element to low light conditions) is usually critical to obtaining sufficient image in such elements. Such elements are typically silver bromoiodide emulsions and may be processed, for example, in known color negative processes such as the Kodak C-41 process as described in The British Journal of Photography Annual of 1988, pages 191–198. If a color negative film element is to be subsequently employed to generate a viewable projection print as for a motion picture, a process such as the Kodak ECN-2 process described in the H-24 Manual available from Eastman Kodak Co. may be employed to provide the color negative image on a transparent support. Color negative development times are typically 3' 15" or less and desirably 90 or even 60 seconds or less.

Another type of color negative element is a color print. Such an element is designed to receive an image optically printed from an image capture color negative element. A color print element may be provided on a reflective support for reflective viewing (e.g. a snap shot) or on a transparent support for projection viewing as in a motion picture. Elements destined for color reflection prints are provided on a reflective support, typically paper, employ silver chloride emulsions, and may be optically printed using the so-called negative-positive process where the element is exposed to light through a color negative film which has been processed as described above. The print may then be processed to form a positive reflection image using, for example, the Kodak RA-4 process as generally described in PCT WO 87/04534 or U.S. Pat. No. 4,975,357. Color projection prints may be processed, for example, in accordance with the Kodak ECP-2 process as described in the H-24 Manual. Similarly, back-lit image transparencies may be prepared for display purposes. Color print development times are typically 90 seconds or less and desirably 45 or even 30 seconds or less.

The above emulsions are typically sold with instructions to process using the appropriate method such as the mentioned color negative (Kodak C-41), color print (Kodak RA-4), or reversal (Kodak E-6) process.

Preferred color developing agents are p-phenylenediamines such as:

- 4-amino-N,N-diethylaniline hydrochloride,
- 4-amino-3-methyl-N,N-diethylaniline hydrochloride,
- 4-amino-3-methyl-N-ethyl-N-(2-methanesulfonamido-ethyl)aniline sesquisulfate hydrate,
- 4-amino-3-methyl-N-ethyl-N-(2-hydroxyethyl)aniline sulfate,
- 4-amino-3-(2-methanesulfonamido-ethyl)-N,N-diethylaniline hydrochloride and
- 4-amino-N-ethyl-N-(2-methoxyethyl)-m-toluidine di-p-toluene sulfonic acid.

Development is usually followed by the conventional steps of bleaching, fixing, or bleach-fixing, to remove silver or silver halide, washing, and drying.

The entire contents of the patents and other publications cited in this specification are incorporated herein by reference.

SYNTHESIS EXAMPLE

Preparation of Coupler I1

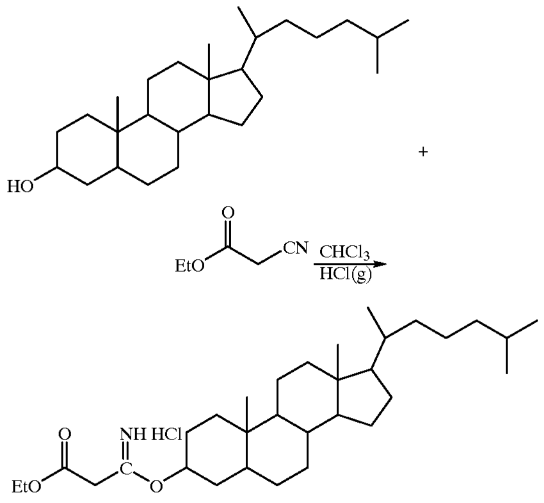

Cholestanol (50 g, 0.12 mol) and ethyl cyanoacetate (14.5 g, 0.12 mol) were mixed in chloroform (300 ml) and the reaction was externally cooled in an ice bath. Hydrogen chloride gas was bubbled into the solution slowly for 2 hrs. The reaction was sealed and placed in a freezer for 3 days. The solid was collected by filtration, washed with cold $Et_2O$ and dried.

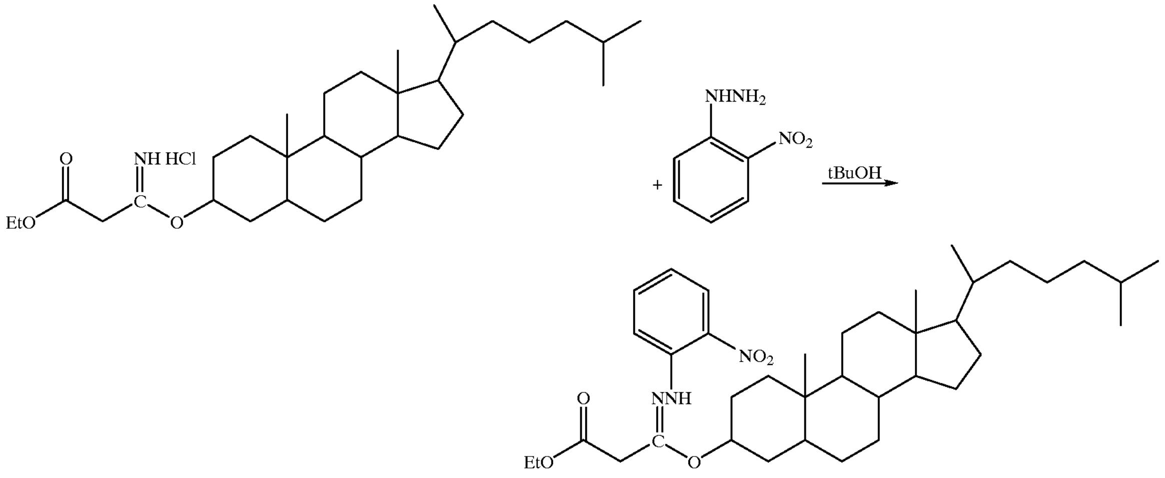

The solid imidate was mixed with ortho nitrophenylhydrazine 15 g,0.1 mol) and stirred at room temperature with a mechanical stirrer for 3 hrs. The reaction was partitioned between ligroin and water. The organic layer was washed with 10% HCl, dried with $MgSO_4$ and concentrated. The red oil residue (35 g) was carried on without further purification.

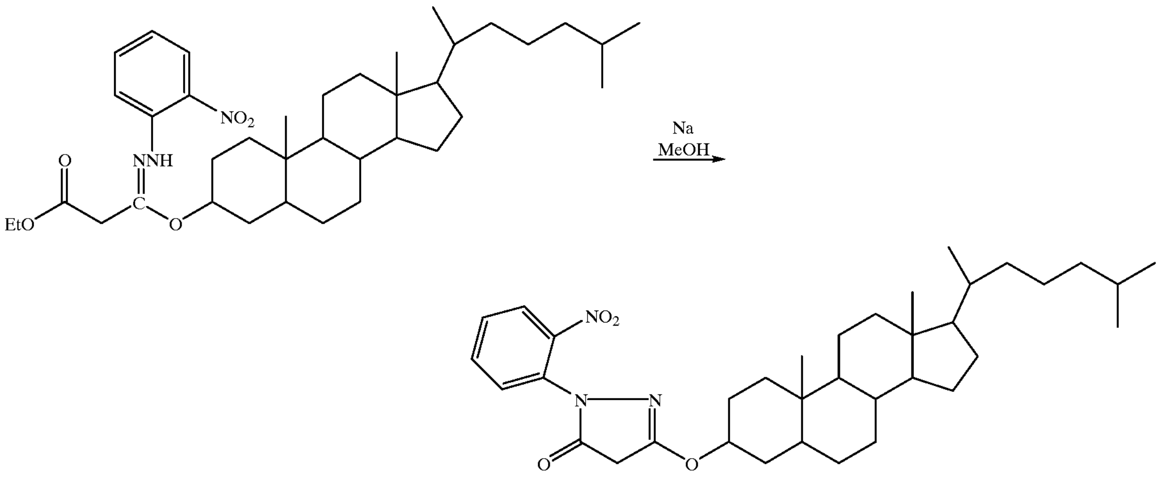

Sodium spheres (4 g, 0.17 mol) was slowly added to methanol and stirred at room temperature until a clear solution was obtained. The red oil for the previous reaction was added in one portion and the reaction was stirred for 2 hrs at room temperature. The reaction was concentrated and the residue was partitioned between EtOAc and 10% HCl. The organic layer was dried ($MgSO_4$)and concentrated to a solid. This material was recrystallized from heptane to give 25 g of product.

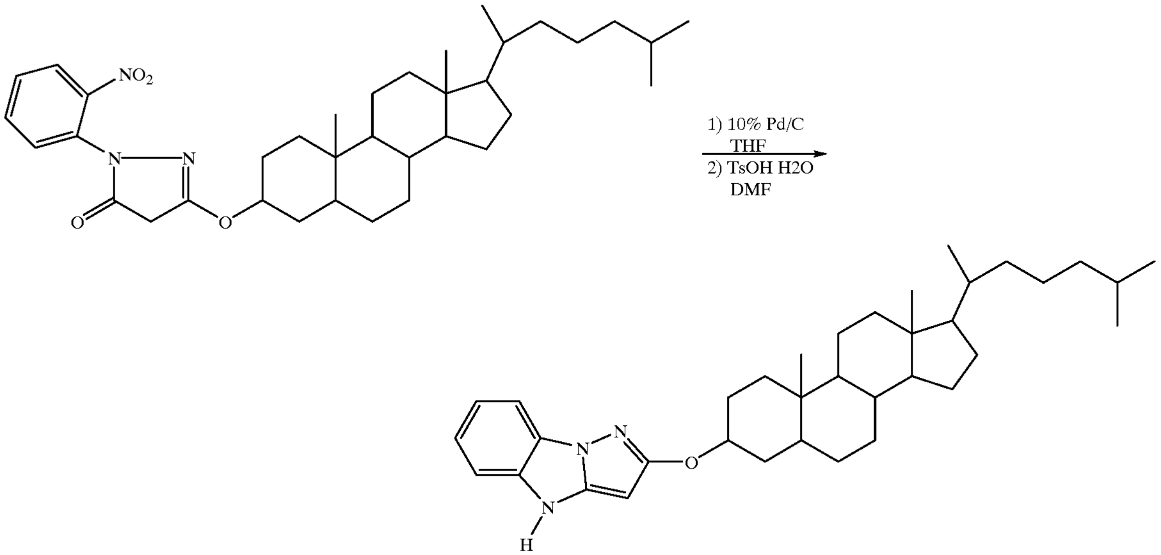

The nitro pyrazolone (25 g) was dissolved in tetrahydrofuran, treated with 2 g of 10% palladium on carbon and shaken with hydrogen at 50 psi for 24 hours. The reaction was filtered and concentrated. The product was dissolved in dimethylformamide and treated with 4 g of toluene sulfonic acid mono-hydrate and heated on a steam bath for 24 hrs. The reaction was partitioned between EtOAc and $H_2O$. The organic layer was washed with $H_2O$, dried ($MgSO_4$) and concentrated. The solid residue was chromatographcd to give 10 g of product.

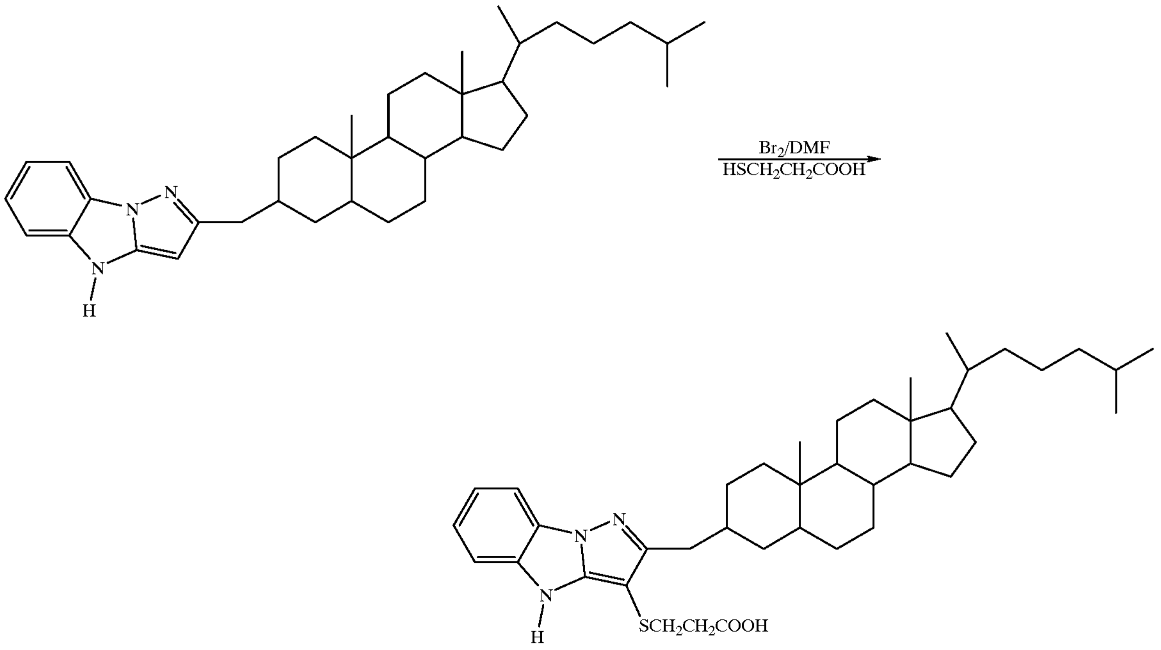

The benzpyrazoloimidazole (10 g) and 3-mercaptopropionic acid (4 ml) were dissolved in dimethylformamide (50 ml) and treated dropwise with a solution of bromine (3.6 g) in dimethylformamide (10 ml). The reaction was stirred for 3 hrs at RT and partitioned between EtOAc and $H_2O$. The organic layer was washed with water twice and dried ($MgSO_4$) and concentrated. The solid product was recrystallized twice from acetonitrile to give 7 g of product.

PHOTOGRAPHIC EXAMPLES

Dispersions of the couplers were prepared as below. In one vessel, the coupler, coupler solvent, stabilizer(s), and ethyl acetate were combined and warmed to dissolve. To this solution was added gelatin, surfactant, and water. After manual mixing the mixture was passed three times through a Gaulin colloid mill.

The photographic elements were prepared by coating the following layers in the order listed on a resin-coated paper support:

| | | |
|---|---|---|
| 1st layer | | |
| Gelatin | 3.23 | g/m$^2$ |
| 2nd layer | | |
| Gelatin | 1.83 | g/m$^2$ |
| Coupler | 0.53 | mmol/m$^2$ |
| Dibutylphthalate | 0.54 | g/m$^2$ |
| Stabilizer A | 0.27 | g/m$^2$ |
| Stabilizer B | 0.27 | g/m$^2$ |
| Green sensitized AgCl emulsion | 0.17 | g/m$^2$ |
| 3rd layer | | |
| Gelatin | 1.34 | g/m$^2$ |
| 2-(2H-benzotriazol-2-yl)-4,6-bis-(1,1-dimethyl-propyl)phenol | 0.73 | g/m$^2$ |
| Tinuvin 326 ™ (Ciba-Geigy) | 0.13 | g/m$^2$ |
| Hexanoic acid,2-ethyl-,1 ,4-cyclohexanediyl bis(methylene)ester | 0.29 | g/m$^2$ |
| 1,4-Benzenediol,2,5-bis (1,1,3,3-tetramethylbutyl)- | 0.18 | g/m$^2$ |
| 4th layer | | |
| Gelatin | 1.40 | g/m$^2$ |
| Bis(vinylsulfonylmethyl)ether | 0.14 | g/m$^2$ |

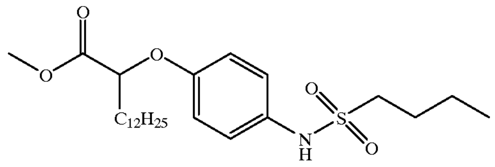

Stabilizer A

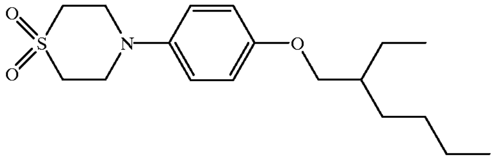

Stabilizer B

The photographic elements were given stepwise exposures to green light and processed as follows at 35° C.:

| | |
|---|---|
| Developer | 45 seconds |
| Bleach-Fix | 45 seconds |
| Wash (running water) | 1 minute, 30 seconds |

The developer and bleach-fix were of the following compositions:

| | | |
|---|---|---|
| Developer | | |
| Water | 700.00 | mL |
| Triethanolamine | 12.41 | g |
| Blankophor REU™ (Mobay Corp.) | 2.30 | g |
| Lithium polystyrene sulfonate (30%) | 0.30 | g |
| N,N-Diethylhydroxylamine (85%) | 5.40 | g |
| Lithium sulfate | 2.70 | g |
| N-{2-[(4-amino-3-methylphenyl) ethylamino]ethyl }methane sulfonamidesesquisulfate | 5.00 | g |
| 1-Hydroxyethyl-1,1-diphosphonic acid (60%) | 0.81 | g |
| Potassium carbonate, anhydrous | 21.16 | g |
| Potassium chloride | 1.60 | g |
| Potassium bromide | 7.00 | mg |
| Water to make 1.00 L | | |
| pH @ 26.7° C. adjusted to 10.04 +/− 0.05 | | |

-continued

| | | |
|---|---|---|
| Bleach-Fix | | |
| Water | 700.00 | mL |
| Solution of ammonium thiosulfate (54.4%) + ammonium sulfite (4%) | 127.40 | g |
| Sodium metabisulfite | 10.00 | g |
| Acetic acid (glacial) | 10.20 | g |
| Solution of ammonium ferric ethylenediaminetetraacetate (44%) + ethylenediaminetetraacetic acid (3.5%) | 110.40 | g |
| Water to make | 1.00 | L |
| pH @ 26.7° C. adjusted to 5.50 +/− 0.10 | | |

Magenta dyes were formed upon processing. The following photographic characteristics were determined: $D_{max}$ (the maximum density to green light); Speed (the relative log exposure required to yield a density to green light of 1.0); and Contrast (the ratio (S−T)/0.6, where S is the density at a log exposure 0.3 units greater than the Speed value and T is the density at a log exposure 0.3 units less than the Speed value).

The combination of this invention provide comparable and acceptable values for $D_{max}$ Contrast, Speed, and other photographic properties when they are coated, exposed in a controlled manner, and processed as above.

The 2-substituent of the invention also improves the thermal yellowing of the areas where no magenta dye is formed during processing. Table I contains Status A Blue Dmin density changes that are observed from processed strips when they are subject to a high temperature of 75° C. and high relative humidity of 50%.

TABLE I

| Sample | Coupler | Type | 2 wk 75° C./ 50% RH Yellowing |
|---|---|---|---|
| 1 | C1 | Comp | 0.19 |
| 2 | I1 | Inv | 0.04 |
| 3 | I1 | Inv | 0.04 |
| 4 | C1 | Comp | 0.22 |
| 5 | C2 | Comp | 0.06 |
| 6 | C3 | Comp | 0.06 |
| 7 | C4 | Comp | 0.07 |
| 8 | C1 | Comp | 0.21 |
| 9 | C5 | Comp | 0.23 |
| 10 | C6 | Comp | 0.24 |

As the data demonstrates, the resistance to yellowing is greatly improved when the photogenic element includes a coupler of the type described in the invention having an alkoxy susstituent in the 2-position bearing a substituent of three or more fused rings.

The following comparison compounds were employed:

C1

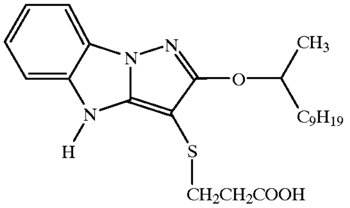

-continued

C2

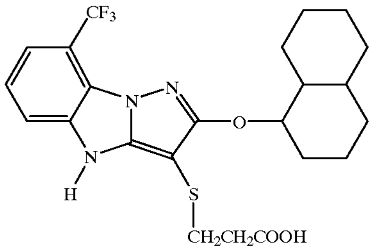

C3

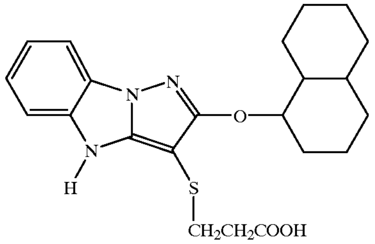

C4

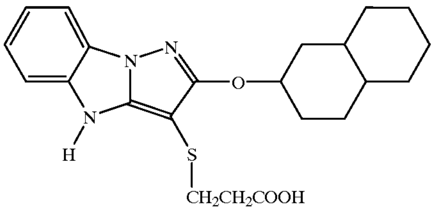

C5

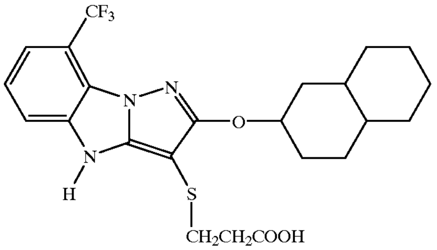

C6

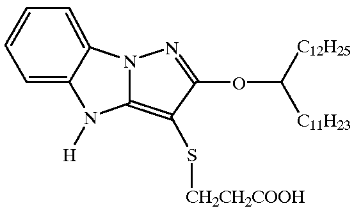

What is claimed is:

1. A photographic element comprising a light-sensitive silver halide emulsion layer having associated therewith a 4-H-pyrazolo-[1,5-a] benzimidazole coupler bearing in the 2-position an alkoxy substituent containing a substituent comprising at least 3 fused carbocyclic rings.

2. The element of claim 1 wherein the coupler has Formula I:

I

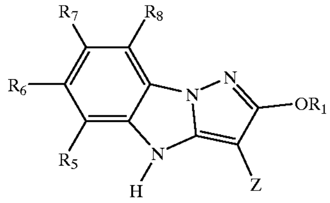

wherein:

$R_1$ is an alkyl group branched at the alpha carbon and contains a substituent comprising three or more fused rings;

$R_5$, $R_6$, $R_7$, and $R_8$ are each independently a hydrogen atom or a substituent; and Z is H or a coupling-off group.

3. The element of claim 1 wherein the substituent comprising at least 3 fused rings contains a phenanthrene group.

4. The element of claim 3 wherein the phenanthrene group is a steroid group.

5. The element of claim 2 in which $R_1$ is a secondary, tertiary, or cyclic alkyl group.

6. The element of claim 2 in which each of $R_5$, $R_6$, $R_7$, and $R_8$ is a hydrogen atom.

7. The element of claim 2 in which Z is a substituted alkylthio group.

8. The element of claim 2 in which Z is an N heterocycle.

9. A photographic element comprising a support on which is coated at least one blue-sensitive silver halide emulsion layer having associated therewith at least one yellow dye-forming coupler, at least one green-sensitive silver halide emulsion as described in claim 1, and at least one red-sensitive silver halide emulsion layer having associated therewith at least one cyan dye-forming coupler.

10. The element of claim 9 wherein the silver halide content of the green-sensitized silver halide emulsion layer comprises at least 90 mole % silver chloride.

11. The element of claim 1 wherein the support is a reflective support.

12. The element of claim 1 wherein the dispersed in a high-boiling solvent and the mole ratio of solvent to coupler is in excess of 1.

13. The element of claim 12 wherein the mole ratio of solvent to coupler is in excess of 2.

14. The element of claim 1 which is designed for direct viewing by reflective, projection or back-lit means.

15. The element of claim 14 comprising a transparent support.

16. The element of claim 2 wherein the coupler of formula (I) is selected from the following:

I1
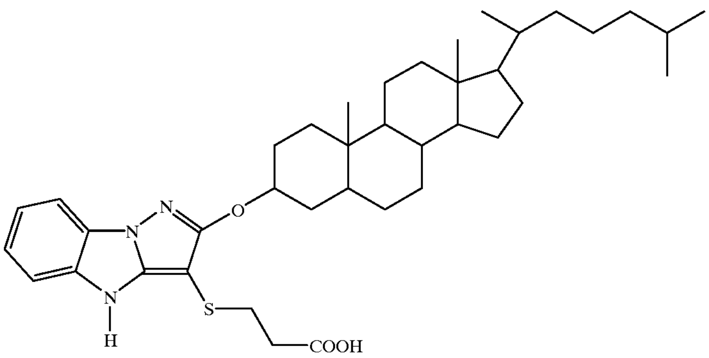
I2
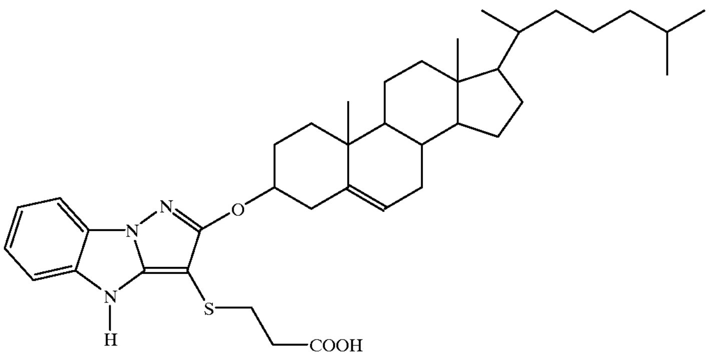
I3
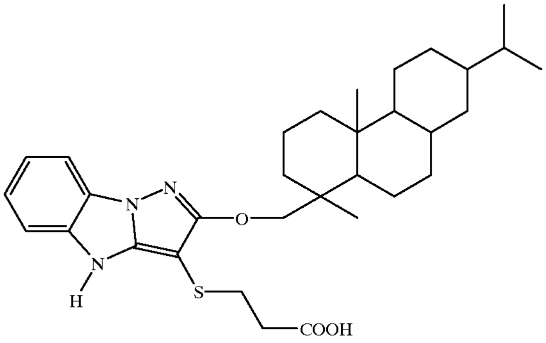
I4
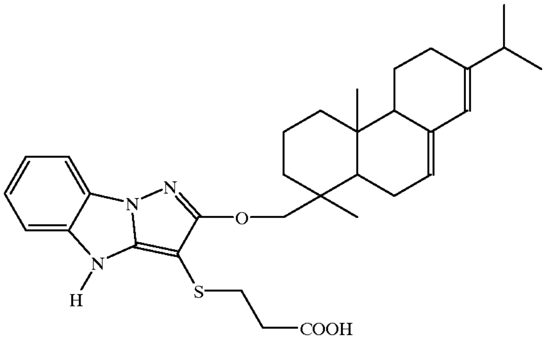

-continued
I5
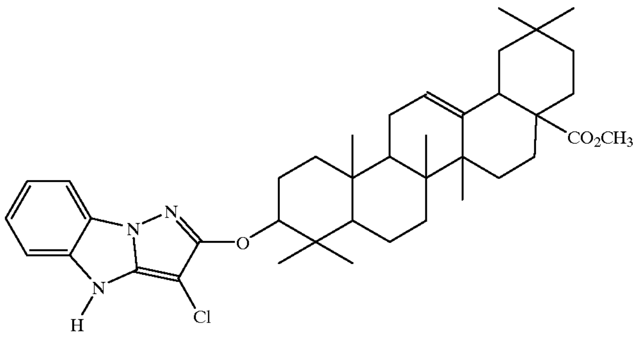
I6
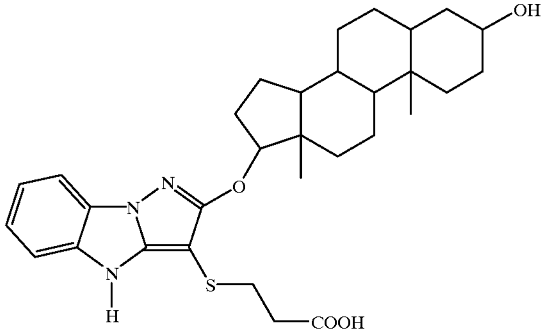
I7
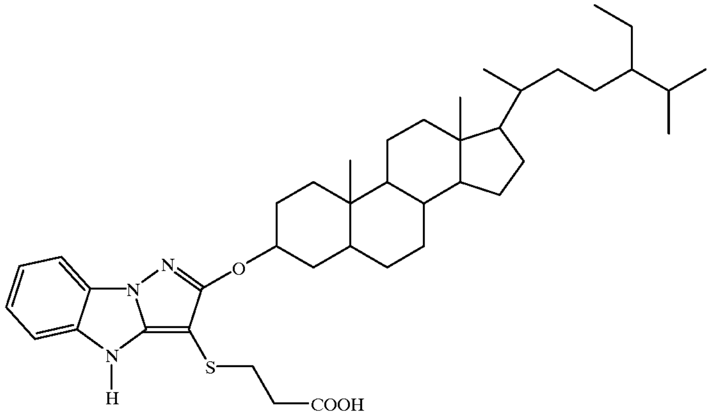
I8
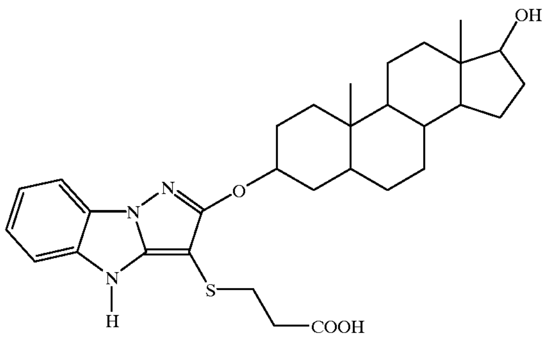

-continued
I9
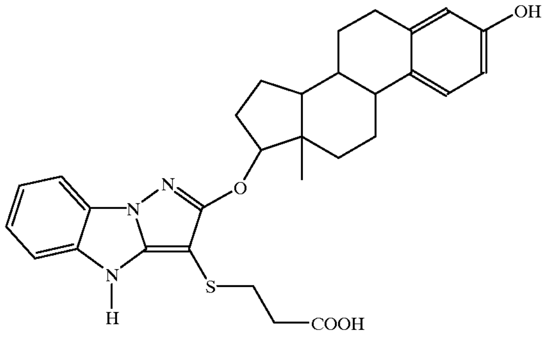
I10
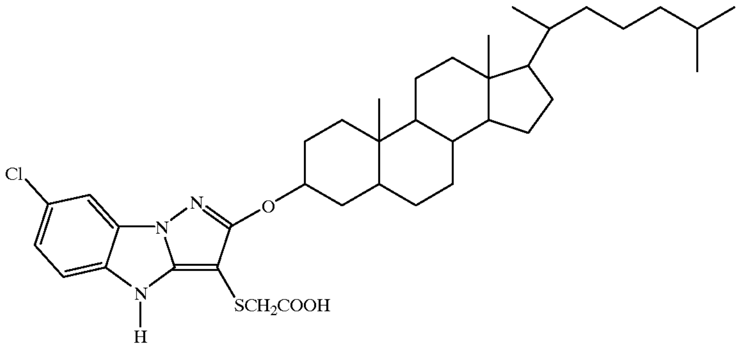
I11
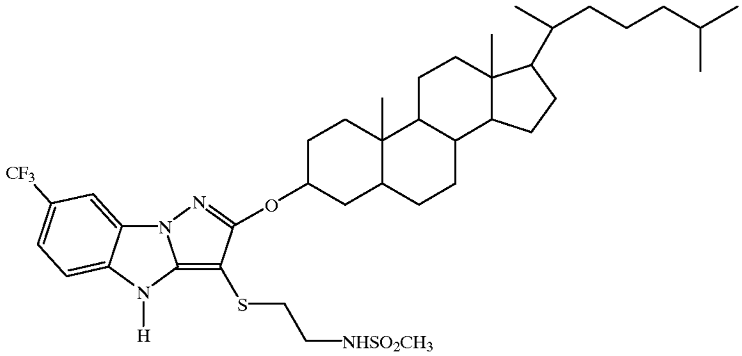
I12
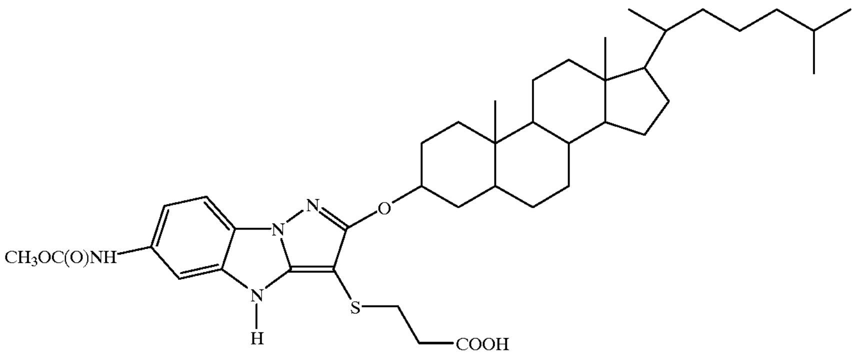

-continued
I13
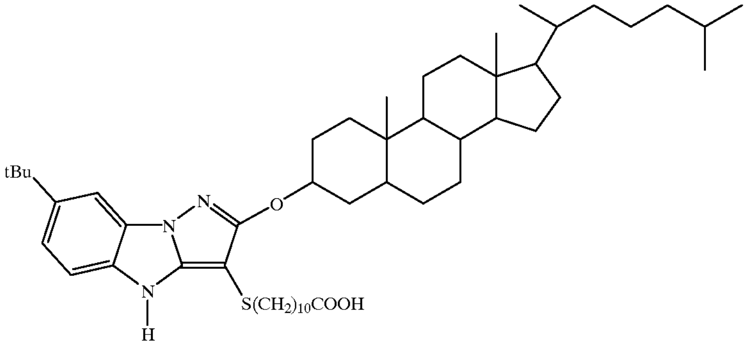
and
I14
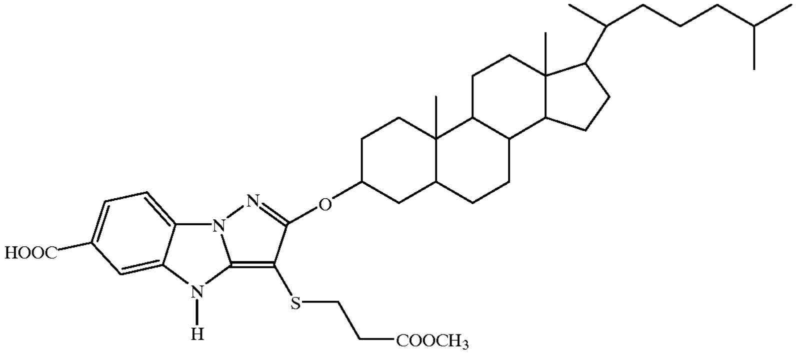
* * * * *